United States Patent
Gavard Molliard

(10) Patent No.: US 8,455,465 B2
(45) Date of Patent: *Jun. 4, 2013

(54) HEAT STERILISED INJECTABLE COMPOSITION OF HYALURONIC ACID OR ONE OF THE SALTS THEREOF, POLYOLS AND LIDOCAINE

(75) Inventor: Samuel Gavard Molliard, Bogeve (FR)

(73) Assignee: Anteis S.A., Plan-les-Ouates, Geneva (CH)

( * ) Notice: Subject to any disclaimer, the term of this patent is extended or adjusted under 35 U.S.C. 154(b) by 224 days.

This patent is subject to a terminal disclaimer.

(21) Appl. No.: 13/119,787

(22) PCT Filed: Nov. 4, 2009

(86) PCT No.: PCT/FR2009/052134
§ 371 (c)(1),
(2), (4) Date: Mar. 18, 2011

(87) PCT Pub. No.: WO2010/052430
PCT Pub. Date: May 14, 2010

(65) Prior Publication Data
US 2011/0201571 A1  Aug. 18, 2011

(30) Foreign Application Priority Data

Nov. 7, 2008 (FR) ..................... 08 57575

(51) Int. Cl.
*A01N 43/04* (2006.01)
*A61K 31/70* (2006.01)
*A61K 31/715* (2006.01)
*A61K 9/14* (2006.01)

(52) U.S. Cl.
USPC ............................. 514/62; 514/54; 424/488

(58) Field of Classification Search
USPC ...................... 514/62, 54; 424/488
See application file for complete search history.

(56) References Cited

U.S. PATENT DOCUMENTS

| | | | |
|---|---|---|---|
| 2002/0019339 A1* | 2/2002 | Naughton | 514/2 |
| 2006/0122147 A1 | 6/2006 | Wohlrab | |
| 2006/0246137 A1 | 11/2006 | Hermitte et al. | |
| 2007/0077292 A1* | 4/2007 | Pinsky | 424/450 |
| 2007/0196426 A1 | 8/2007 | Hermitte et al. | |
| 2010/0226988 A1 | 9/2010 | Lebreton | |
| 2010/0316683 A1 | 12/2010 | Piron et al. | |
| 2011/0230438 A1* | 9/2011 | Bos | 514/54 |

FOREIGN PATENT DOCUMENTS

| | | |
|---|---|---|
| WO | 98/41171 A1 | 9/1998 |
| WO | 0046252 A1 | 8/2000 |
| WO | 2004/032943 A1 | 4/2004 |
| WO | 2004/092222 A2 | 10/2004 |
| WO | 2005/012364 A2 | 2/2005 |
| WO | 2005/085329 A1 | 9/2005 |
| WO | 2007/077399 A2 | 7/2007 |
| WO | 2008/068297 A1 | 6/2008 |

OTHER PUBLICATIONS

Wahl, G.: "European evaluation of a new hyaluronic acid filler incorporating lidocaine", Journal of Cosmetic Dermatology, vol. 7, Nov. 6, 2008, pp. 298-303.
International Search Report, dated Aug. 26, 2010, from corresponding PCT application.

* cited by examiner

*Primary Examiner* — Scarlett Goon
(74) *Attorney, Agent, or Firm* — Young & Thompson

(57) ABSTRACT

An injectable aqueous composition of hyaluronic acid or one of the salts thereof, one or more polyol(s) and lidocaine is used for cosmetic purposes or for therapeutic purposes. It has improved viscoelastic rheological properties and long in vivo persistence. The polyol is chosen, for example, from glycerol, sorbitol, propylene glycol, mannitol, erythritol, xylitol, maltitol and lactitol. The particular properties are obtained by heat sterilizing the mixture.

13 Claims, No Drawings

HEAT STERILISED INJECTABLE COMPOSITION OF HYALURONIC ACID OR ONE OF THE SALTS THEREOF, POLYOLS AND LIDOCAINE

BACKGROUND OF THE INVENTION

The invention relates to an injectable aqueous composition in the form of a gel based on hyaluronic acid or one of the salts thereof, on one or more polyol(s) and on lidocaine, said heat-sterilized composition having improved viscoelastic rheological properties and long in vivo persistence, for use for cosmetic purposes or for therapeutic purposes.

Hyaluronic acid-based injectable gels have been used for many years, for cosmetic purposes, for filling or replacing biological tissues (filling wrinkles, remodeling of the face, increasing lip volume, etc.) and also in treatment to rehydrate the skin by mesotherapy.

Hyaluronic acid-based injectable gels are also used in many therapeutic applications. For example,
- in rheumatology, as an agent for replacement or for temporary supplementation of synovial fluid,
- in urology/gynecology, as an agent for increasing sphincter volume or urethral volume,
- in ophthalmology, as an adjuvant to cataract surgery or for treating glaucoma,
- in pharmaceutics, as an agent for release of active substances,
- in surgery, for bone reconstruction, increasing vocal cord volume or producing surgical tissues.

A great deal of effort has been made to improve the physicochemical stability of hyaluronic acid-based gels in order to increase their in vivo persistence (i.e. the residence time of the gel at the injection site) and thus to increase the duration of treatment effectiveness.

DESCRIPTION OF THE PRIOR ART

According to the prior art, the increasing of the persistence of hyaluronic acid-based gels and therefore of their resistance to the various in vivo degradation factors is essentially carried out by means of hyaluronic acid crosslinking and/or grafting techniques. For example,
- WO 2005/012364 describes gels based on crosslinked and grafted polysaccharides, including hyaluronic acid, which have better persistence than the noncrosslinked and/or nongrafted products.
- WO 2004/092222 describes gels based on polysaccharides, including hyaluronic acid, containing at least one low-molecular-weight polysaccharide and at least one high-molecular-weight polysaccharide, said gels having a greater persistence than that of products which do not have a mixture of molecular weights.
- WO 2005/085329 describes a method of production for obtaining gels based on polydensified crosslinked hyaluronic acid, said gels having a long in vivo persistence.
- WO 2000/0046252 describes gels based on hyaluronic acid with strong "biostability" having a high degree of crosslinking by virtue of a process for double crosslinking hyaluronic acid.

Polyols belong to a family of molecules of chemical formula $C_xH_yO_z$ which have at least two alcohol groups. By virtue of the high capacity of said polyols for adjusting osmolarity, those skilled in the art know that they can introduce polyols into an injectable aqueous formulation in order to obtain an iso-osmolar composition.

Lidocaine (or lidocaine hydrochloride) is a local anesthetic commonly used in the cosmetic and medical fields. This molecule has in particular been used for many years in products for cosmetic purposes, such as products for filling wrinkles, in order to limit pain during and after injection (in the case of the product Zyderm® containing collagen and 0.3% lidocaine).

The prior art describes hyaluronic acid-based gels which may contain a polyol and/or lidocaine. For example,
- WO 2007/077399 describes gels based on hyaluronic acid and on a viscous biocompatible alcohol, the sterilization of which increases the viscosity.
- WO 2004/032943 describes hyaluronic acid-based gels containing local anesthetics, including lidocaine.
- WO 98/41171 describes an injectable composition in the form of a gel based on hyaluronic acid, mannitol and lidocaine.
- WO 2008/068297 describes the use of a subcutaneously or intradermally injectable implant in the form of a hyaluronic acid hydrogel. It also discloses the use of mannitol as an antioxidant.
- European evaluation of a new hyaluronic acid filler incorporating lidocaine, G. WAHL, *Journal of Cosmetic Dermatology*, vol. 7, 6 Nov. 2008, pages 298-303, describes a formulation for dermatological use comprising hyaluronic acid and lidocaine.

SUMMARY OF THE INVENTION

It has now been discovered that the addition of a polyol and of lidocaine to a gel based on hyaluronic acid, regardless of whether it is noncrosslinked or crosslinked, grafted or nongrafted, or crosslinked and grafted, followed by heat-sterilization of this formulation, makes it possible to obtain (compared with a polyol-free and lidocaine-free gel):
- a very large improvement in the rheological properties of the gel,
- an improvement in the persistence of the gel by countering the three major types of degradation of a hyaluronic acid-based gel in vivo (enzymatic degradation by hyaluronidases, free-radical degradation, thermal degradation at 37° C.),
- an improvement in the rheological stability of the gel over time and therefore a product shelf-life that may be extended.

It has in fact been shown that, entirely surprisingly, the addition of one or more polyol(s) and of lidocaine to a hyaluronic acid-based gel:
- does not modify the rheological properties of the gel before heat sterilization,
- considerably modifies the rheological properties of the gel after heat sterilization (compared with a polyol-free and lidocaine-free gel).

In other words, before heat sterilization, the viscoelastic properties of a hyaluronic acid-based gel with polyol and lidocaine are identical to those of a polyol-free and lidocaine-free hyaluronic acid-based gel.

After heat sterilization, the viscoelastic properties of a hyaluronic acid-based gel with polyol and lidocaine are different than those of a polyol-free and lidocaine-free hyaluronic acid-based gel. The gel with polyol and lidocaine has a very strong elasticity (higher G') and a more elastic viscoelastic nature (lower Tan δ) compared with a polyol-free and lidocaine-free gel.

Heat sterilization profoundly modifies the structure of the gel and therefore the viscoelastic properties thereof (decrease in rheological parameters G' and G"/increase in the parameter Tan δ). It is noted that the presence of a polyol and of lidocaine in a hyaluronic acid-based gel considerably modifies the change in the rheological parameters during heat sterilization (limitation of the change in rheological parameters: decrease in G' and in G" significantly less strong/increase in Tan δ significantly less strong).

By limiting the degradation of the hyaluronic acid-based gel during heat sterilization, the structure of the hyaluronic acid-based gel with polyol and lidocaine is different than that obtained with a polyol-free and lidocaine-free hyaluronic acid-based gel. This structure has in particular a reinforced elastic nature (better ability of the gel to create volume).

This better resistance to thermal degradation confers in particular on the gel a better product stability at ambient temperature over time. Thus, a product produced according to this invention will have a shelf-life that may be extended compared with a product not containing polyol and lidocaine.

It has also been shown that a hyaluronic acid-based gel with polyol and lidocaine has better resistance to the three degradation factors of a hyaluronic acid-based gel in vivo compared with a polyol-free and lidocaine-free gel:
better resistance to enzymatic degradation,
better resistance to free-radical degradation,
better resistance to thermal degradation.

In particular, the improvement in the resistance to thermal and free-radical degradation is entirely noteworthy.

Without wishing to be bound to a theoretical explanation of the effect of the polyol and of the lidocaine against the degradations of a hyaluronic acid-based gel, it is assumed that the lidocaine considerably increases the ability of a polyol to protect a hyaluronic acid-based gel.

Furthermore, the polyol(s) incorporated into the hyaluronic acid-based gel can migrate out of the gel.

Outside the gel, the polyol(s) will be able to be diffused into the tissues and play an important role, for example, in tissue hydration or else by intervening in cellular or biochemical mechanisms.

Finally, the presence of lidocaine in the gel is of major interest for improving the comfort of the patient during and after injection.

Consequently, the injectable aqueous composition based on hyaluronic acid or one of the salts thereof, on one or more polyol(s) and on lidocaine according to the invention has the following advantages for cosmetic purposes or for therapeutic purposes:
better viscoelastic rheological properties of the gel (in particular better ability to create volume) since significantly less degraded at sterilization,
longer in vivo persistence of the gel and therefore a more long-term effect of the treatment by virtue of the action of the polyol(s) and of the lidocaine against the three main types of degradation of the gel in vivo,
better rheological stability of the gel during its shelf-life,
positive action of the polyols on the organism (for example, tissue hydration),
improvement of the comfort of the patient owing to the anesthetizing effect of lidocaine during and after injection.

The invention therefore provides a heat-sterilized injectable composition comprising a gel based on hyaluronic acid or one of the salts thereof, on one or more polyol(s) and on lidocaine.

This composition is used:
for cosmetic purposes for filling biological tissues or for rehydrating the skin by mesotherapy;
for therapeutic purposes such as, for example:

a) in rheumatology, as an agent for replacement or for temporary supplementation of synovial fluid,
b) in urology/gynecology, as an agent for increasing sphincter volume or urethral volume,
c) in ophthalmology, as an adjuvant to cataract surgery or for treating glaucoma,
d) in pharmaceutics, as an agent for release of active substances,
e) in surgery, for bone reconstruction, increasing vocal cord volume or producing surgical tissues.

According to the embodiments of the invention, the gel based on hyaluronic acid or one of the salts thereof is non-crosslinked or crosslinked.

According to the embodiments of the invention, the concentration of hyaluronic acid or of one of the salts thereof is between 0.01 mg/ml and 100 mg/ml and the molecular weight of the hyaluronic acid or one of the salts thereof is between 1000 Da and $10 \times 10^6$ Da.

According to one particular embodiment of the invention, the crosslinking is carried out with bifunctional or polyfunctional molecules chosen from epoxides, epihalohydrins and divinyl sulfone, on hyaluronic acid that is noncrosslinked or already crosslinked with or without one or more other polysaccharides of natural origin.

The various types of hyaluronic acid-based gels are known in the art, and crosslinked and grafted gels are described, for example, in WO 2005/012364.

According to one particular embodiment of the invention, the gel can also contain other biocompatible polymers (such as polysaccharides of natural origin) and/or other active or nonactive substances having a positive effect on the organism or on the gel.

According to the feature of the invention, these gels contain one or more polyol(s) chosen, for example, from glycerol, sorbitol, propylene glycol, xylitol, mannitol, erythritol, maltitol or lactitol.

According to the embodiments of the invention, the polyol concentration in the gel is between 0.0001 and 500 mg/ml and more particularly between 0.0001 and 100 mg/ml.

According to the embodiments of the invention, the lidocaine concentration in the gel is between 0.0001 and 500 mg/ml and more particularly between 0.001 and 50 mg/ml.

According to the embodiments of the invention, the sterilization is carried out with dry or wet heat, preferably with wet heat. Those skilled in the art will be able to select a heat-sterilization cycle (temperature and duration of the sterilization cycle) suitable for the sterilization of their product. For example, the following wet-heat-sterilization cycles can be used: 131° C., 1 min/130° C., 3 min/125° C., 7 min/121° C., 20 min/121° C., 10 min/100° C., 2 h.

EXAMPLES

Examples are proposed in order to illustrate the invention but they in no way limit said invention. The formulations prepared in the following examples are gels based on crosslinked sodium hyaluronate (NaHA) with or without polyol and lidocaine in a buffered aqueous solution at pH=7.

The crosslinked gels are prepared according to techniques well known to those skilled in the art. The sodium hyaluronate used to produce these gels has a molecular weight equal to $2.5 \times 10^6$ Da. The crosslinking agent used is butanediol diglycidyl ether (BDDE) and the definition of the degree of crosslinking used is: weight (BDDE)/weight (dry NaHA).

The incorporation of the polyol into the gel is carried out by adding the necessary amount of polyol (% expressed by weight) to the gel and mixing with a spatula for 10 minutes (for 50 g of final gel).

The incorporation of the lidocaine into the gel is carried out by adding the necessary amount of lidocaine (% expressed by weight) to the gel and mixing with the spatula for 10 minutes (for 50 g of final gel).

In order to have strictly identical production conditions for the gels with and without polyol and lidocaine, the polyol-free and lidocaine-free crosslinked gel is also mixed with a spatula for 10 minutes (for 50 g of final gel).

The gels prepared are packed into a glass syringe and then heat-sterilized (121° C., 10 min).

The rheometer used to carry out the rheological characterizations is an AR2000 (TA instruments) with a plate geometry of 40 mm, a gap of 1000 μm and an analysis temperature of 37° C.

Example 1

Demonstration by rheology of the difference in structure after heat sterilization between hyaluronic acid-based gels with and without polyol/lidocaine Take A, a gel based on crosslinked NaHA (NaHA molar mass=$2.5 \times 10^6$ Da, NaHA concentration=22.5 mg/ml, degree of crosslinking=9%). The gel is then purified by dialysis for 24 hours (regenerated cellulose, separation limit: molar mass=60 kDa). 150 g of purified gel is mixed with a spatula for 10 minutes.

The resulting gel is divided up into three fractions of equal weight (50 g).

Take B, fraction No. 1. 1% of glycerol, 1.5% of sorbitol and 0.3% of lidocaine are added to this fraction. The gel is mixed with a spatula for 10 minutes.

Take C, fraction No. 2. 1% of glycerol and 1.5% of sorbitol are added to this fraction. The gel is mixed with a spatula for 10 minutes.

Take D, fraction No. 3. A solution of NaCl of appropriate concentration is added in order to have a hyaluronic acid concentration and an osmolarity which are equivalent to those of gels B and C. The gel is mixed with a spatula for 10 minutes.

Take B, C and D, the gels resulting from fractions B, C and D respectively.

The resulting gels have a pH close to 7.00, an osmolarity close to 300 mOsm/kg and an equivalent hyaluronic acid concentration.

A rheology measurement (frequency sweep—0.01 to 100 Hz) is carried out for each of the gels B, C and D before sterilization.

A comparison of the values of G' (=elastic modulus), G" (=viscous modulus) and Tan δ=G"/G' is carried out at 1 Hz.

| Formulation | G' (1 Hz) (Pa) | G" (1 Hz) (Pa) | Tan δ (1 Hz) |
|---|---|---|---|
| Gel B (before sterilization) | 316 | 94 | 0.297 |
| Gel C (before sterilization) | 314 | 93 | 0.296 |
| Gel D (before sterilization) | 318 | 94 | 0.296 |

No rheological differences, and therefore no difference in structure, are observed between the three gels B, C and D before sterilization.

The gels B, C and D are packed into a 1 ml glass syringe and are then wet-heat-sterilized at 121° C. for 10 minutes.

A rheology measurement (frequency sweep—0.01 to 100 Hz) is carried out for each of the gels B, C and D after sterilization.

A comparison of the values of G' (=elastic modulus), G" (=viscous modulus) and Tan δ=G"/G' is carried out at 1 Hz.

| Formulation | G' (1 Hz) (Pa) | G" (1 Hz) (Pa) | Tan δ (1 Hz) |
|---|---|---|---|
| Gel B (after sterilization) According to the invention | 128 | 62 | 0.484 |
| Gel C (after sterilization) | 91 | 47 | 0.516 |
| Gel D (after sterilization) | 75 | 50 | 0.667 |

Considerable rheological differences, and therefore considerable structural differences, are observed between the three gels B, C and D after heat sterilization.

After heat sterilization, the gel according to the invention (=gel B) displays a significantly superior elasticity (higher G') and elastic nature (lower Tan δ) than the polyol-free and lidocaine-free gel (=gel D).

The presence of the polyols and of the lidocaine make it possible to greatly limit the thermal degradation of the hyaluronic acid-based gel during heat sterilization.

| Formulation | Variation G' (1 Hz) before/after sterilization |
|---|---|
| Gel B According to the invention | −59% |
| Gel C | −71% |
| Gel D | −76% |

Example 2

Demonstration of the better resistance to enzymatic degradation of a hyaluronic acid-based gel with polyol and lidocaine.

The resistance to enzymatic degradation of the gel B according to the invention (see example 1) is compared with that of the gel D (see example 1).

The degradation test is carried out using an AR2000 rheometer (TA instruments) with a plate geometry of 40 mm and a gap of 1000 μm.

The degradation test is carried out by adding a solution of hyaluronidases to the test gel, homogenizing with the spatula for 1 minute, placing the whole at a temperature of 37° C. and imposing a deformation of 0.3%. The value of the parameter G' at 1 Hz is measured at t=5 min and t=40 min.

| Formulation | G' (1 Hz) (Pa) At t = 5 min | G' (1 Hz) (Pa) At t = 40 min | ΔG' (1 Hz) |
|---|---|---|---|
| Gel B (sterile) According to the invention | 115 | 52 | −55% |
| Gel D (sterile) | 60 | 24 | −60% |

It is noted that the gel according to the invention has better resistance to enzymatic degradation.

Example 3

Demonstration of the better resistance to free-radical degradation of a hyaluronic acid-based gel with polyol and lidocaine.

The resistance to free-radical degradation of the gel B according to the invention (see example 1), of the gel C (see example 1) and of the gel D (see example 1) is compared.

The degradation test is carried out using an AR2000 rheometer (TA instruments) with a plate geometry of 40 mm and a gap of 1000 μm.

The degradation test is carried out by adding an oxidizing agent to the test gel, homogenizing with the spatula for 1 minute, placing the whole at a temperature of 37° C. and imposing a deformation of 0.3%. The value of the parameter G' at 1 Hz is measured at t=5 min and t=40 min.

| Formulation | G' (1 Hz) (Pa) At t = 5 min | G' (1 Hz) (Pa) At t = 40 min | ΔG' (1 Hz) |
|---|---|---|---|
| Gel B (sterile) According to the invention | 122 | 98 | −20% |
| Gel C (sterile) | 80 | 38 | −53% |
| Gel D (sterile) | 58 | 20 | −66% |

It is noted that the gel according to the invention has a much better resistance to free-radical degradation.

Example 4

Demonstration of the better resistance to thermal degradation of a hyaluronic acid-based gel with polyol and lidocaine.

The resistance to thermal degradation of the gel B according to the invention (see example 1) and of the gel D (see example 1) is compared.

The thermal degradation test is carried out by introducing the test gel into an incubator at 80° C. for 8 hours and measuring the value of the parameter G' (1 Hz) at t=0 and at t=8 days.

| Formulation | G' (1 Hz) (Pa) At t = 0 | G' (1 Hz) (Pa) At t = 8 days | ΔG' (1 Hz) |
|---|---|---|---|
| Gel B (sterile) According to the invention | 128 | 66 | −48% |
| Gel D (sterile) | 75 | 29 | −61% |

It is noted that the gel according to the invention has better resistance to thermal degradation.

Example 5

Demonstration of the Better Rheological stability at ambient temperature over time of a hyaluronic acid-based gel with polyol and lidocaine.

The gel B according to the invention (see example 1) and the gel D (see example D) were stored at ambient temperature (25° C.) for 8 months.

The value of the parameter G' (1 Hz) was measured at t=0, t=4 months and t=8 months.

| Formulation | Gel B (sterile) According to the invention | Gel D (sterile) |
|---|---|---|
| G' (1 Hz) (Pa) At t = 0 | 128 | 75 |
| G' (1 Hz) (Pa) At t = 4 months | 126 | 68 |
| G' (1 Hz) (Pa) At t = 8 months | 120 | 66 |
| ΔG' (1 Hz) (0-8 months) | −6% | −12% |

It is noted that the gel according to the invention has better rheological stability at ambient temperature over time.

The invention claimed is:

1. An injectable aqueous composition in the form of a gel, used for cosmetic purposes or for therapeutic purposes, comprising cross-linked hyaluronic acid or one of the salts thereof, one or more polyol(s) selected from the group consisting of glycerol, sorbitol, mannitol, propylene glycol, erythritol, xylitol, maltitol and lactitol, and lidocaine, which has undergone heat sterilization, the effects of which are improved viscoelastic rheological properties and improved in vivo persistence compared to gels without said polyols and lidocaine.

2. The injectable aqueous composition as claimed in claim 1, wherein the sterilization is carried out with humid heat.

3. The injectable aqueous composition as claimed in claim 1, wherein the hyaluronic acid or one of the salts thereof is crosslinked with or without one or more other polysaccharides of natural origin.

4. The injectable aqueous composition as claimed in claim 1, wherein the hyaluronic acid or one of the salts thereof is crosslinked with bifunctional or polyfunctional molecules selected from the group consisting of epoxides, epihalohydrins and divinyl sulfone.

5. The injectable aqueous composition as claimed in claim 1, wherein the concentration of hyaluronic acid or of one of the salts thereof is between 0.01 mg/ml and 100 mg/ml, and the molecular weight of the hyaluronic acid or one of the salts thereof is between 1000 Da and $10 \times 10^6$ Da.

6. The injectable aqueous composition as claimed in claim 1, wherein the polyol concentration is between 0.0001 and 100 mg/ml.

7. The injectable aqueous composition as claimed in claim 1, wherein the lidocaine concentration is between 0.0001 and 50 mg/ml.

8. A method for filling or replacing biological tissues in a patient in need thereof, comprising injecting the injectable aqueous composition of claim 1 into said patient.

9. A method for filling wrinkles, remodeling of the face or increasing lip volume in a patient in need thereof, comprising injecting the injectable aqueous composition of claim 1 into wrinkles, face or lips of said patient.

10. A method for treating rehydration of the skin of a patient by mesotherapy, comprising injecting the injectable aqueous composition of claim 1 into the skin of said patient.

11. A method for separating, replacing or filling a biological tissue or increasing the volume of said tissue in a patient in need thereof, comprising injecting the injectable aqueous composition of claim 1 into said patient.

12. A method for replacement or for temporary supplementation of synovial fluid in a patient in need thereof, comprising injecting the injectable aqueous composition as claimed in claim 1 into said patient.

13. The injectable aqueous composition as claimed in claim 1, used in a field selected from the group consisting of:
urology/gynecology, as an agent for increasing sphincter volume or urethral volume;
ophthalmology, as an adjuvant to cataract surgery or for treating glaucoma;
pharmaceutics, as an agent for release of active substances; and
surgery, for bone reconstruction, increasing vocal cord volume or producing surgical tissues.

* * * * *